US012661046B2

(12) United States Patent
Zhao et al.

(10) Patent No.: US 12,661,046 B2
(45) Date of Patent: Jun. 23, 2026

(54) SYSTEM, METHOD AND APPARATUS FOR OBJECTIVELY SCREENING DEPRESSION

(71) Applicant: Yongxiang Zhao, Fuzhou City (CN)

(72) Inventors: Yongxiang Zhao, Fuzhou City (CN);
Lianmeng Zhang, Fuzhou City (CN)

(73) Assignee: Yongxiang Zhao, Fuzhou City (CN)

( * ) Notice: Subject to any disclaimer, the term of this patent is extended or adjusted under 35 U.S.C. 154(b) by 208 days.

(21) Appl. No.: 18/730,169

(22) PCT Filed: Dec. 31, 2021

(86) PCT No.: PCT/CN2021/143746
§ 371 (c)(1),
(2) Date: Jul. 18, 2024

(87) PCT Pub. No.: WO2023/087512
PCT Pub. Date: May 25, 2023

(65) Prior Publication Data
US 2025/0134429 A1      May 1, 2025

(30) Foreign Application Priority Data

Nov. 18, 2021    (CN) .......................... 202111372211.4

(51) Int. Cl.
*A61B 5/16* (2006.01)
*A61B 5/0205* (2006.01)
(Continued)

(52) U.S. Cl.
CPC ............ *A61B 5/165* (2013.01); *A61B 5/0205* (2013.01); *A61B 5/318* (2021.01); *G16H 50/30* (2018.01);
(Continued)

(58) Field of Classification Search
CPC ...... A61B 5/165; A61B 5/02405; A61B 5/318
See application file for complete search history.

(56) References Cited

U.S. PATENT DOCUMENTS

| 2013/0066395 A1* | 3/2013 | Simon .................. A61B 5/4094 |
| | | 607/48 |
| 2022/0117556 A1* | 4/2022 | Kranck .................. A61B 5/681 |

FOREIGN PATENT DOCUMENTS

| CN | 104127194 A | * | 11/2014 |
| CN | 204274481 U | * | 4/2015 |

(Continued)

OTHER PUBLICATIONS

Peng. Junlin et al.—A Preliminary Study on Resting Heart Rate in Predicting Early Depression and Cognition Function after Ischemic Stroke; Journal of Xuzhou Medical University; vol. 40, No. 12, Dec. 31, 2020 (Dec. 31, 2020), ISSN: 2096-3882, text, pp. 905-906.
(Continued)

*Primary Examiner* — Eric D. Bertram
(74) *Attorney, Agent, or Firm* — Schmeiser, Olsen & Watts LLP

(57)        ABSTRACT

A system for objectively screening depression is provided. The system includes an ECG signal acquisition device configured to acquire ECG signals of a subject when the subject completes test processes, wherein the test processes include: normal breathing in a first posture, deep breathing in the first posture, normal breathing in a second posture, and deep breathing in the second posture, the first posture and the second posture incudes any of the following: lying posture, sitting posture, standing posture; an integration and calculation device configured to obtain the ECG signals, and integrate and calculate the ECG signals to obtain heart rate parameters and HRV characteristic parameters in the test processes; and a depression risk assessment device configured to input the heart rate parameters and the HRV characteristic parameters in each test process into a depression screening model to obtain a depression risk index of the subject.

8 Claims, 3 Drawing Sheets

(51) Int. Cl.

| | | |
|---|---|---|
| *A61B 5/318* | (2021.01) | |
| *G16H 50/30* | (2018.01) | |
| *A61B 5/024* | (2006.01) | |
| *A61B 5/0245* | (2006.01) | |
| *A61B 5/08* | (2006.01) | |

(52) U.S. Cl.
CPC ......... *A61B 5/02405* (2013.01); *A61B 5/0245* (2013.01); *A61B 5/08* (2013.01)

(56) References Cited

FOREIGN PATENT DOCUMENTS

| | | | | | |
|---|---|---|---|---|---|
| CN | 107802273 | A | 3/2018 | | |
| CN | 113069116 | A | 7/2021 | | |
| CN | 113509183 | A | 10/2021 | | |
| CN | 112057087 | B | * 4/2022 | ......... | A61B 5/02405 |
| KR | 20130050817 | A | 5/2013 | | |
| WO | 2013016290 | A2 | 1/2013 | | |

OTHER PUBLICATIONS

Kuang, Danni—Assisted Diagnosis Technology of Depression Using Heart Rate Variability; Chinese Doctoral Dissertations and Master's Theses Full-text Database (Master), Medicine & Public Health; No. 02, Feb. 15, 2020 (Feb. 15, 2020).

Chen, Xiuwen et al. "Heart rate variability in patients with major depression disorder during a clinical autonomic test" Psychiatry Research, vol. 256, Jun. 14, 2017 (Jun. 14, 2017).

International Search Report for PCT/CN2021/143746, mailed on Aug. 19, 2022.

Written Opinion for PCT/CN2021/143746, mailed on Aug. 19, 2022.

International Report on Patentability for PCT/CN2021/143746, mailed on May 30, 2024.

Lulu Zhao; Depression status detection based on dynamic characteristic analysis of multiphysiology signal; Chinese Excellent Doctoral dissertates Full text Database (Doctor) Medical and Health Science and Technology series, No. 11, 17-52, 73-93.

* cited by examiner

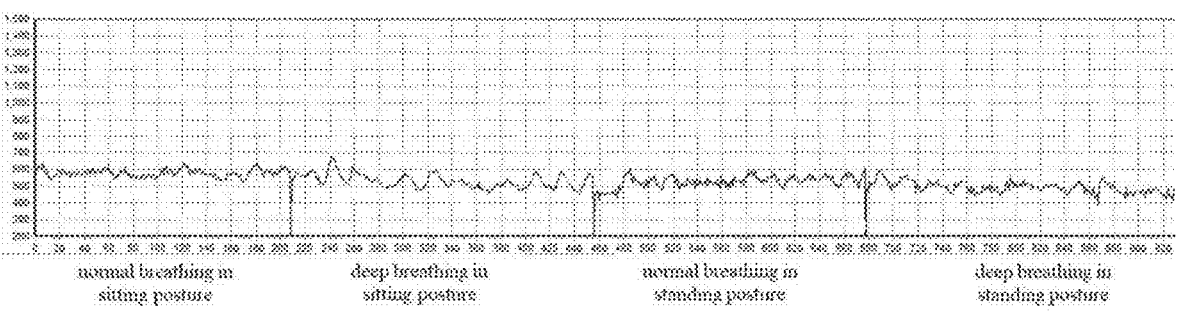

normal breathing in        deep breathing in        normal breathing in        deep breathing in
sitting posture            sitting posture          standing posture           standing posture

FIG. 4

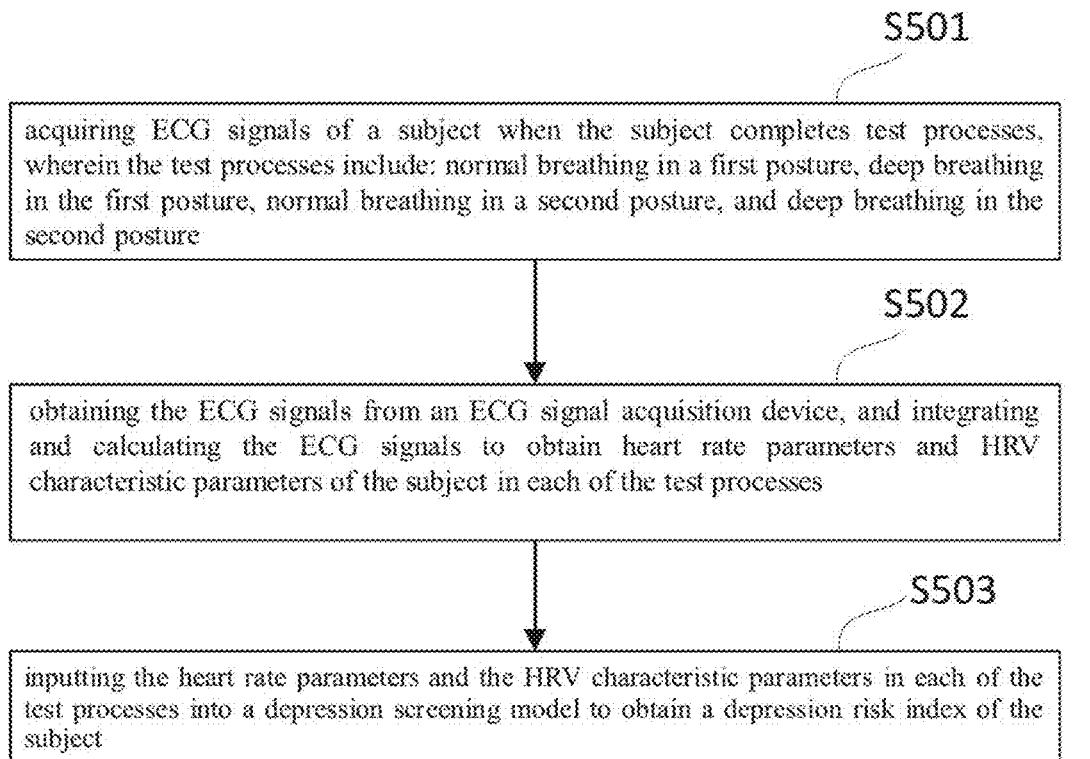

S501 acquiring ECG signals of a subject when the subject completes test processes, wherein the test processes include: normal breathing in a first posture, deep breathing in the first posture, normal breathing in a second posture, and deep breathing in the second posture

S502 obtaining the ECG signals from an ECG signal acquisition device, and integrating and calculating the ECG signals to obtain heart rate parameters and HRV characteristic parameters of the subject in each of the test processes

S503 inputting the heart rate parameters and the HRV characteristic parameters in each of the test processes into a depression screening model to obtain a depression risk index of the subject

FIG. 5

SYSTEM, METHOD AND APPARATUS FOR OBJECTIVELY SCREENING DEPRESSION

CROSS-REFERENCE TO RELATED APPLICATION

This application is a national application of PCT/CN2021/143746 filed on Dec. 31, 2021, which claims priority to Chinese Patent Application No. 202111372211.4 filed on Nov. 18, 2021, the entire contents both of which is hereby incorporated by reference.

FIELD OF TECHNOLOGY

The following relates to the technical field of signal recognition and processing, and in particular to a system, a method and an apparatus, an electronic device and a storage medium for objectively screening depression.

BACKGROUND

Depression is the most common depressive disorder, with significant and persistent low mood as a main clinical feature, and is a main type of mood disorders. There are currently about 300 million depression patients in the world, and its harm has exceeded that of seemingly "more deadly" diseases such as cardiovascular and cerebrovascular diseases, diabetes, cancer and the like.

Depression is not a hereditary disease, nor is it caused by introversion. It is more like a "severe cold" in the brain.

At present, there are three main ways for identifying and diagnosing clinical depression:

The first is to rely on a doctor's subjective judgment, mainly the doctor uses a depression assessment scale for screening. The depression assessment scale is a tool for measuring depression. It was developed by Professor William W. K. Zung at Duke University in 1965-1966. It includes 20 items, each of which consists of seven levels of scoring, including two items of mental-affective symptoms, eight items of somatic disorders, two items of psychomotor disorders, and eight items of depressive psychological disorders. The depression assessment scale is easy to use and can intuitively reflect subjective feelings of depressed patients. It is suitable for adults with depressive symptoms. However, it is difficult to assess a depression level of those with severe retardation symptoms. In addition, the depression assessment scale is not very effective for people with low cultural level or slightly lower intelligence level, and the process requires patients to have a high degree of cooperation. Since the measurement results of the scale options come from subjective answers of the patients, it is easy for patients to deliberately avoid options.

The second is to evaluate by collecting biological information of the patients. Gamma band of EEG in people with depressive disorders shows a phenomenon of continuous enhancement. People with depressive disorders have an increase in asymmetry of an activation level of prefrontal lobe of the brain. This process assesses patient's depression level by collecting the patient's electroencephalogram (EEG), functional magnetic resonance imaging (fMRI) and other technologies. However, this process is relatively expensive and has a low accuracy due to weak EEG signals.

The third is to evaluate by collecting the patient's electrocardiogram (ECG) signals. In a study of patients with severe depression diagnosed according to DSM-IV-TR criteria, it was shown that depression is associated with changes in cardiac autonomic nerve tone, with decreased parasympathetic nerve activity and increased sympathetic nerve activity, which leads to the following conclusion: a common neurobiological dysfunction may cause depression and cardiac autonomic changes in diseases. According to the study, a method of judging a depression level by collecting ECG signals is proposed. In embodiments, the method conducts 4 tests on patients, namely, resting test: keep sitting and breathe normally; deep exhalation test: inhale for 5 seconds, exhale for 5 seconds, repeat 6 times; Valsalva action: inhale and hold breath for 15 seconds, exhale forcefully and relax for 15 seconds, repeat 3 times; standing test: stand normally and avoid body movements. In the above 4 processes, a number of ECG signals are collected by a measuring instrument, and each ECG signal is compared with a pre-set normal value. Clinicians evaluate the patient's depression level based on comparison results. However, the above judgment process is to judge ECG signal indicators in different test stages separately, and it needs to use big data samples. Since heart rate signals of each patient are different, the evaluation method has low an evaluation accuracy and poor robustness.

SUMMARY

An aspect relates to a system, a method and an apparatus for objectively screening depression, an electronic device and a storage medium. By adopting innovative test methods and steps, the present application provides more accurate, robust and adaptable assessment results of depression compared with traditional test methods and steps.

Embodiments of the present application are implemented through the following technical solutions. In a first aspect, an embodiment of the present application provides a system for objectively screening depression, including:

an electrocardiogram (ECG) signal acquisition device configured to acquire ECG signals of a subject when the subject completes test processes, wherein the test processes include: normal breathing in a first posture, deep breathing in the first posture, normal breathing in a second posture, and deep breathing in the second posture;

an integration and calculation device configured to obtain the ECG signals from the ECG signal acquisition device, and integrate and calculate the ECG signals to obtain heart rate parameters and HRV characteristic parameters of the subject in each of the test processes, wherein the HRV characteristic parameters include at least one of the following: time domain parameters, frequency domain parameters, and nonlinear parameters; and a depression risk assessment device configured to input the heart rate parameters and the HRV characteristic parameters in each of the test processes into a depression screening model to obtain a depression risk index of the subject.

In some embodiments, the first posture includes any one of the following: lying posture, sitting posture, standing posture; the second posture includes any one of the following: lying posture, sitting posture, standing posture; and the first posture is different from the second posture.

In some embodiments, the test processes further include: normal breathing in a third posture, and deep breathing in the third posture; the third posture includes any of the following: lying posture, sitting posture, standing posture; and the third posture is different from the first posture and the second posture.

In some embodiments, the depression screening model is configured to perform a first data comparison between the heart rate parameters and the HRV characteristic parameters in each of the test processes and sample data in a preset database, to obtain a first risk index according to each abnormal first comparison result, and to obtain the depression risk index of the subject according to the first risk index.

In some embodiments, the heart rate parameters include: a first heart rate parameter detected and obtained when the subject completes the normal breathing in the first posture; a second heart rate parameter detected and obtained when the subject completes the deep breathing in the first posture; a third heart rate parameter detected and obtained when the subject completes the normal breathing in the second posture; a fourth heart rate parameter detected and obtained when the subject completes the deep breathing in the second posture; the HRV characteristic parameters include: a first HRV characteristic parameter detected and obtained when the subject completes the normal breathing in the first posture; a second HRV characteristic parameter detected and obtained when the subject completes the deep breathing in the first posture;

a third HRV characteristic parameter detected and obtained when the subject completes the normal breathing in the second posture; a fourth HRV characteristic parameter detected and obtained when the subject completes the deep breathing in the second posture; the depression screening model is also configured to obtain deviation data obtained by at least one of the following comparisons: the second heart rate parameter and the first heart rate parameter, the third heart rate parameter and the first heart rate parameter, the fourth heart rate parameter and the second heart rate parameter, the fourth heart rate parameter and the third heart rate parameter, the second HRV characteristic parameter and the first HRV characteristic parameter, the third HRV characteristic parameter and the first HRV characteristic parameter, the fourth HRV characteristic parameter and the second HRV characteristic parameter, the fourth HRV characteristic parameter and the third HRV characteristic parameter; the depression screening model is configured to perform a second data comparison between at least one of the deviation data and sample data in the preset database; the depression screening model is further configured to obtain a second risk index according to each abnormal second comparison result, and to obtain the depression risk index of the subject according to the first risk index and the second risk index.

In some embodiments, the system further includes a breathing detection device including a breathing detection module, wherein the breathing detection module is configured to detect breathing data of the subject during the test processes.

In some embodiments, the system further includes an action standardization scoring device that is connected to the breathing detection device, and is configured to obtain calm relaxation degree of the subject in each normal breathing test stage and breathing synchronization rate of the subject in each deep breathing test stage according to the breathing data, and to obtain an action standardization score of the subject in each test stage according to the calm relaxation degree and/or the breathing synchronization rate.

In some embodiments, the each abnormal first comparison result includes that the first comparison result is greater than and/or less than a set threshold;

the each abnormal second comparison result includes that the second comparison result is greater than and/or less than a set threshold.

In some embodiments, the ECG signal acquisition device includes a sensor, an ECG signal processing circuit and an AD sampling circuit connected in sequence, the sensor is configured to connect to the subject and acquire the ECG signals of the subject when the subject completes test processes, the ECG signal processing circuit is integrated with a filter amplifier for filtering the ECG signals sent by the sensor, and the ECG signals after filtering are converted into digital signals by the AD sampling circuit and sent to the integration and calculation device;

the integration and calculation device includes a first data interface, a first processor and a first memory, the first processor is configured to drive the first data interface to receive the ECG signals, and to store the ECG signals in the first memory, and the first processor is further configured to integrate and calculate the ECG signals; the depression risk assessment device includes a second data interface, a second processor and a second memory, the second processor is configured to drive the second data interface to receive the heart rate parameters and the HRV characteristic parameters, and store the heart rate parameters and the HRV characteristic parameters in the second memory, and the second processor is further configured to input the heart rate parameters and the HRV characteristic parameters in each of the test processes into the depression screening model; the time domain parameters include at least one of the following: MEAN_HR, MAX_HR, MIN_HR, STD_HR, MEAN, SDNN, SDSD, RMSSD, average NN, NN50, PNN50, NN20, PNN20, RANGE_NNI, CVSD and CVNNI;

the frequency domain parameters include at least one of the following: VLF, LF, HF, TP, pVLF, pLF, pHF, nLF, nHF and LF/HF; the nonlinear parameters include at least one of the following: SD1, SD2, SD2/SD1, α1, α2, Lyapunov exponent, complexity parameters, correlation dimension parameters and entropy parameters; wherein, the complexity parameters include at least one of the following: C0 complexity, C1 complexity, C2 complexity; wherein, the correlation dimension parameters include at least one of the following: number of phase points, embedding dimension, delay time; wherein, the entropy parameters include at least one of the following: sample entropy, approximate entropy, fuzzy entropy.

According to a second aspect, the present application provides a method of objectively screening depression, including, acquiring electrocardiogram (ECG) signals of a subject when the subject completes test processes, wherein the test processes include: normal breathing in a first posture, deep breathing in the first posture, normal breathing in a second posture, and deep breathing in the second posture; obtaining the ECG signals from an ECG signal acquisition device, and integrating and calculating the ECG signals to obtain heart rate parameters and HRV characteristic parameters of the subject in each of the test processes, wherein the HRV characteristic parameters include at least one of the following: time domain parameters, frequency domain parameters, and nonlinear parameters; and inputting the heart rate parameters and the HRV characteristic parameters in each of the test processes into a depression screening model to obtain a depression risk index of the subject.

According to a third aspect, the present application provides an apparatus for objectively screening depression, including, an electrocardiogram (ECG) signal acquisition module configured to acquire ECG signals of a subject when the subject completes test processes, wherein the test processes include: normal breathing in a first posture, deep breathing in the first posture, normal breathing in a second posture, and deep breathing in the second posture; an integration and calculation module configured to obtain the ECG signals from the ECG signal acquisition module, and integrate and calculate the ECG signals to obtain heart rate parameters and HRV characteristic parameters of the subject in each of the test processes, wherein the HRV characteristic parameters include at least one of the following: time domain parameters, frequency domain parameters, and non-linear parameters; and a depression risk index acquisition module configured to input the heart rate parameters and the HRV characteristic parameters in each of the test processes into a depression screening model to obtain a depression risk index of the subject.

According to a fourth aspect, the present application provides an electronic device, including at least one memory and at least one processor; and a computer program stored in the memory and executable by the processor, wherein the processor implements following steps when executing the computer program: acquiring electrocardiogram (ECG) signals of a subject when the subject completes test processes, wherein the test processes include: normal breathing in a first posture, deep breathing in the first posture, normal breathing in a second posture, and deep breathing in the second posture; obtaining the ECG signals from an ECG signal acquisition device, and integrating and calculating the ECG signals to obtain heart rate parameters and HRV characteristic parameters of the subject in each of the test processes, wherein the HRV characteristic parameters include at least one of the following: time domain parameters, frequency domain parameters, and nonlinear parameters; and inputting the heart rate parameters and the HRV characteristic parameters in each of the test processes into a depression screening model to obtain a depression risk index of the subject.

According to a fifth aspect, the present application provides a storage medium storing a computer instruction program, wherein, when the computer instruction program is executed by a processor, the processor implements following steps: acquiring electrocardiogram (ECG) signals of a subject when the subject completes test processes, wherein the test processes include: normal breathing in a first posture, deep breathing in the first posture, normal breathing in a second posture, and deep breathing in the second posture; obtaining the ECG signals from an ECG signal acquisition device, and integrating and calculating the ECG signals to obtain heart rate parameters and HRV characteristic parameters of the subject in each of the test processes, wherein the HRV characteristic parameters include at least one of the following: time domain parameters, frequency domain parameters, and nonlinear parameters; and inputting the heart rate parameters and the HRV characteristic parameters in each of the test processes into a depression screening model to obtain a depression risk index of the subject.

In the embodiments of the present application, innovative test methods and steps make it easier for patients to standardize an operation, with good repeatability and standardization, and may be completed by everyone. In addition, compared with a traditional method of evaluating depression level by relying on a single indicator in each test stage, which requires a large amount of big data samples, has a low classification accuracy and poor robustness, the embodiment of the present application only needs a small amount of data samples to obtain a very high judgment and classification accuracy. Although each person's heart rate signal is different, the embodiment of the present application combines comparative change trend of each person between each test stage to make a more accurate assessment of the depression level of the subject, and all test actions may be automatically judged by the sensor whether the action is standardized, with strong robustness and wide adaptability.

In order to more clearly explain the technical solutions in the embodiments of the present application or the conventional art, the drawings required to be used in description of the embodiments or the conventional art will be briefly introduced below. Obviously, the drawings described below are only some embodiments of the present application. For a person skilled in the art, other drawings may be obtained based on these drawings without creative work.

BRIEF DESCRIPTION

Some of the embodiments will be described in detail, with references to the following Figures, wherein like designations denote like members, wherein:

FIG. 4 is a schematic diagram of a heart rate spectrum of a depression patient;

FIG. 5 is a schematic diagram of a process of a method of objectively screening depression according to an embodiment.

DETAILED DESCRIPTION

Figure 1:
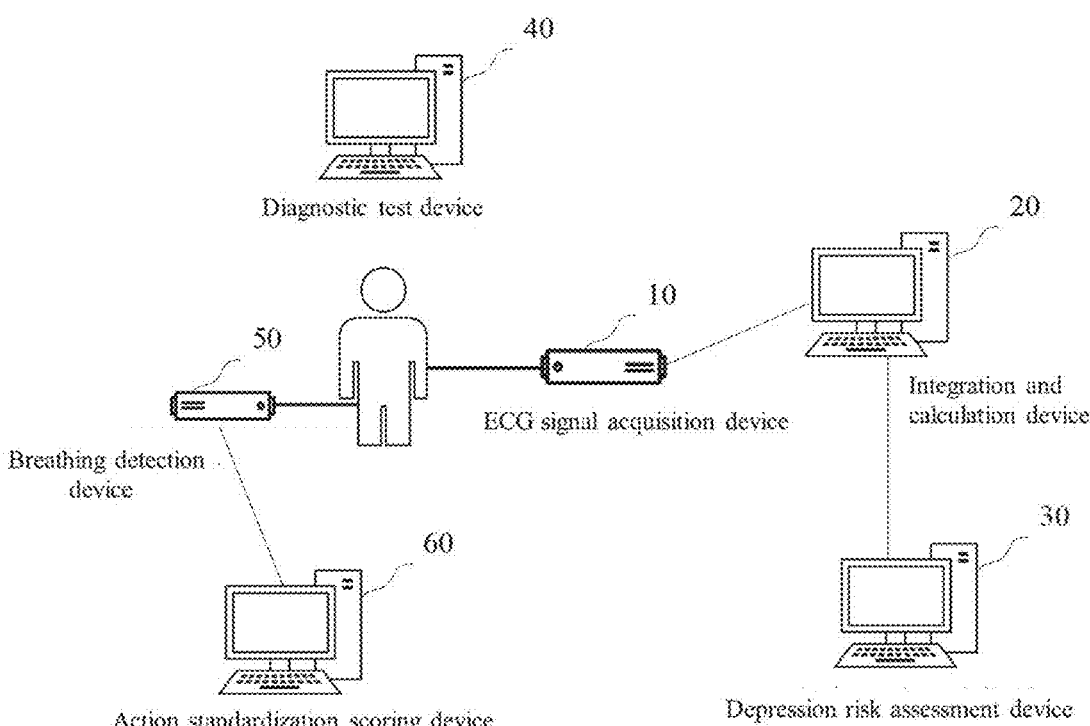
FIG. 1 is a schematic structural diagram of a system for objectively screening depression according to an embodiment.

In order to make the purpose, technical solutions and advantages of the present application clearer, embodiments of the present application will be described in detail below with reference to the accompanying drawings.

It should be clear that the described embodiments are only part of the embodiments of the present application, not all of the embodiments. Based on the embodiments in the present application, all other embodiments obtained by a person skilled in the art without creative work are within the scope of protection of the embodiments of the present application.

Terms used in the embodiments of the present application are only for the purpose of describing specific embodiments and are not intended to limit the embodiments of the present application. Singular forms "a", "an", and "the" used in the embodiments of the present application and appended claims are also intended to include plural forms, unless the context clearly indicates other meanings. It should also be understood that the term "and/or" used herein refers to and includes any or all possible combinations of one or more associated listed items.

When the following description refers to the accompanying drawings, unless otherwise indicated, the same numbers in different drawings represent the same or similar elements. Implementations described in the following exemplary embodiments do not represent all implementations consistent with the present application. On the contrary, they are merely examples of systems and methods consistent with some aspects of the present application as detailed in the appended claims. In the description of the present application, it should be understood that terms "first", "second", "third", etc. are only used to distinguish similar objects, and are not necessarily used to describe a specific order or sequence, nor can they be understood as indicating or implying relative importance. For a person skilled in the art, the specific meanings of the above terms in this application can be understood according to specific circumstances.

In addition, in the description of this application, unless otherwise specified, "plurality" means two or more. "And/or" describes association relationship of associated objects, indicating that three relationships may exist. For example, A and/or B may mean: A exists alone, A and B exist at the same time, and B exists alone. The character "/" generally indicates that the associated objects are in an "or" relationship.

The embodiments of the present application propose a system, a method and an apparatus for objectively screening depression, an electronic device and a storage medium, a screening process thereof includes following six steps: normal breathing in a lying posture, deep breathing in the lying posture, normal breathing in a sitting posture, deep breathing in the sitting posture, normal breathing in a standing posture and deep breathing in the standing posture. Wherein, the above six steps may be performed in sequence according to above arrangement order, or in any other arrangement order, and each step may be performed continuously or after a certain time interval. In addition, only four of the above six steps may be selected to perform, that is, two postures are selected to perform normal breathing and deep breathing respectively. In the embodiments of the present application, four steps of selecting normal breathing in the sitting posture, deep breathing in the sitting posture, normal breathing in the standing posture and deep breathing in the standing posture are used as examples for explanation.

Compared with traditional four steps, namely, a resting test (i.e., normal breathing in the sitting posture), a deep breathing test (i.e., deep breathing in the sitting posture), a Valsalva test (i.e., a breath-holding test for 15 seconds), and a standing test (i.e., normal breathing in the standing posture), changes and innovations made in the embodiments of the present application are as following:

(1) The Valsalva test (i.e., the breath-holding test for 15 seconds) was deleted because most patients cannot perform this test in a standardized manner in practice. It is difficult for middle school students and elderly people to perform this dangerous test. It is tiring to perform this test, and it has poor repeatability, large interference, poor standardization, high difficulty, and a small number of people who can adapt to it.

(2) The deep breathing in the standing posture (i.e., taking a deep breath while in the standing posture, such as 2 minutes, inhaling for 5.5 seconds and exhaling for 5.5 seconds), the normal breathing in the lying posture, and the deep breathing in the lying posture were added.

In the embodiments of the present application, action standardization of a whole test process is good, the action is simple, and with a guidance of video and sound, everyone may complete it in a standardized manner; and the action standardization of new six test steps may be automatically scored and judged by a sensor, and non-standard and sub-standard actions need to be re-tested to improve detection accuracy.

In some embodiments, test time of action in each of the test steps may be between 30 seconds and five minutes, 2 minutes.

Embodiment 1

Directed to technical problems in the background technology, an embodiment of the present application proposes a system for objectively screening depression. As shown in FIG. 1, in embodiments the system includes an electrocardiogram (ECG) signal acquisition device 10, an integration and calculation device 20, a depression risk assessment device 30, a diagnostic test device 40, a breathing detection device 50 and an action standardization scoring device 60.

Wherein, the diagnostic test device 40 is configured to generate and play test steps including test actions according to a preset test program, so that a subject completes multiple preset test actions according to the test steps. The ECG signal acquisition device 10 is configured to acquire ECG signals of the subject during the subject completes the test actions. The integration and calculation device 20 is configured to obtain the acquired ECG signals from the ECG signal acquisition device 10, and to integrate and calculate the ECG signals to obtain heart rate parameters and HRV characteristic parameters of the subject in each of above test processes, wherein the HRV characteristic parameters include at least one of the following: time domain parameters, frequency domain parameters, and nonlinear parameters. The depression risk assessment device 30 is configured to input the heart rate parameters and HRV characteristic parameters in each test process into a depression screening model, and the depression screening model is configured to perform a first data comparison between the heart rate parameters and HRV characteristic parameters in each test process with sample data in a preset database, to obtain a first risk index according to each abnormal first comparison result, and to obtain a depression risk index of the subject according to the first risk index. In some embodiments, the depression risk index may be used to indicate following states of the subject: normal, mild depression, moderate depression and severe depression.

The breathing detection device 50 is configured to detect a breathing state of the subject through a sensor when the subject completes the multiple preset test actions, and to send breathing data to the action standardization scoring device 60. The action standardization scoring device 60 automatically determines whether the subject completes the test actions in a standard manner through an algorithm.

Figure 2:
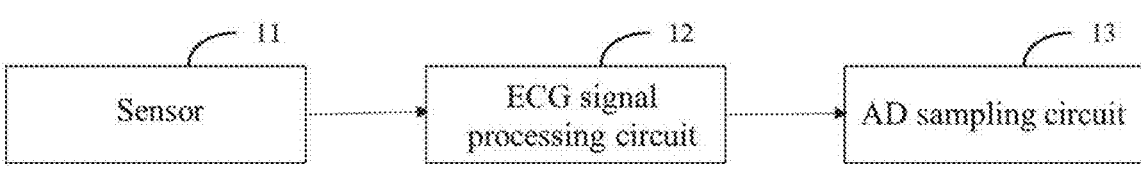
FIG. 2 is a schematic structural diagram of an ECG signal acquisition device 10 according to an embodiment.

In some embodiments, as shown in FIG. 2, the ECG signal acquisition device 10 includes a sensor 11, an ECG signal processing circuit 12, and an AD sampling circuit 13 connected in sequence, wherein the sensor is configured to connect to the subject and acquire the ECG signals of the subject when the subject completes the test actions, and the ECG signal processing circuit 12 is integrated with a filter amplifier for filtering the ECG signals sent by the sensor. The ECG signals after filtering are converted into digital signals by the AD sampling circuit 13 and sent to the integration and calculation device 20.

Wherein, the sensor 11 may be any sensor for measuring heartbeat, and in some examples, may also be a non-contact sensor.

Wherein, the ECG signals are signals of changes of electrical activity generated by each cardiac cycle of the heart recorded from body surface, which is usually recorded in a graphical manner through an electrocardiogram (ECG). In the embodiment of the present application, the acquired ECG signals may be stored in the integration and calculation device 20 in a form of binary data. In other embodiments, other multi-channel synchronous data acquisition devices may be used to acquire and store the ECG signals of the subject.

The ECG signal processing circuit 12 may specifically include a low-pass filter, a band-notch filter and a zero-phase shift filter, wherein the low-pass filter is configured to filter out myoelectric interference, the band-notch filter is configured to eliminate tribute interference, and the zero-phase shift filter is configured to correct baseline drift.

In some embodiments, the integration and calculation device 20 includes a first data interface, a first processor and a first memory. The integration and calculation device 20 may be a computer or other electronic device including the above components. Wherein, the first processor is configured to drive the first data interface to receive the ECG signals acquired by the ECG signal acquisition device 10, and to store the ECG signals in the first memory in the form of binary data. The first processor is further configured to integrate and calculate the ECG signals, so as to obtain the heart rate (HR) parameters and heart rate variability (HRV) characteristic parameters (hereinafter referred to as HRV characteristic parameters) in each of the above test processes.

Wherein, the heart rate is measured in beats per minute, which refers to number of heart beats per minute of the subject, also called resting heart rate, which is generally 60 to 100 beats per minute, and may have individual differences due to age, gender or other physiological factors. Heart rate variability refers to change in difference between successive heartbeat cycles, or change in a speed of the heartbeat, which is determined by a length of two adjacent R-R intervals, that is, slight difference from a first cardiac cycle to the next cardiac cycle. In the present application, it is not limited to sampling through the R-R interval to obtain the heart rate variability parameters, and it may also be obtained through an N-N interval, or through other methods, such as selecting a specific position in a QRS wave to obtain an interval time between every two heartbeats.

Heart rate variability is used to measure irregularity of the heartbeat. Generally speaking, the irregularity of the heartbeat is dominated by an autonomic nervous system. Therefore, HRV may reflect health of the nervous system. If the heartbeat is more regular, the HRV will be lower. If the heartbeat intervals vary greatly, the HRV will be relatively high. Generally speaking, a high HRV represents a better cardiovascular function and stress resistance, while a low HRV means a higher risk of anxiety and depression.

In embodiments, the HRV characteristic parameters in the embodiment of the present application may include but are not limited to time domain parameters, frequency domain parameters and nonlinear parameters. Wherein, the time domain parameters include but are not limited to: MEAN_HR, MAX_HR, MIN_HR, STD_HR, MEAN, SDNN, SDSD, RMSSD, average NN, NN50, PNN50, NN20, PNN20, RANGE_NNI, CVSD and CVNNI. Wherein, MEAN_HR is average heart rate during the test; MAX_HR is the maximum heart rate during the test; MIN_HR is the minimum heart rate during the test; STD_HR is standard deviation of the heart rate during the test; MEAN is average of all sinus NN intervals; SDNN is standard deviation of all sinus NN intervals; SDSD is the standard deviation between adjacent NN intervals; RMSSD is root mean square of successive differences between adjacent NN intervals; average NN is average of two adjacent NN intervals; NN50 is number of adjacent NN interval differences with an absolute value greater than 50 ms in a calculation cycle; PNN50 is percentage of adjacent NN interval differences with an absolute value greater than 50 ms; NN20 is number of adjacent NN interval differences with an absolute value greater than 20 ms in a calculation cycle; PNN20 is percentage of adjacent NN interval differences with an absolute value greater than 20 ms; RANGE_NNI is mean of all adjacent NN intervals; CVSD is standard deviation of the coefficient of variation of the NN intervals; and CVNNI is the coefficient of variation of the NN intervals.

Frequency domain parameters include but are not limited to: VLF, LF, HF, TP, pVLF, pLF, pHF, nLF, nHF and LF/HF. Wherein, VLF is power of the very low frequency component of 0.0033-0.04 Hz, LF is the power of the low frequency component of 0.04-0.15 Hz; HF is the power of the high frequency component of 0.15-0.4 Hz; TP is the total power; pVLF is percentage of the very low frequency component of a heart rate variability curve; pLF is the percentage of the low frequency component of the heart rate variability curve; pHF is the percentage of the high frequency component of the heart rate variability curve; nLF is normalized low frequency power, $nLF=LF/(TP-VLF)*100\%$; nHF is normalized high frequency component, $nHF=HF/(TP-VLF)*100\%$; and LF/HF is a ratio of the low frequency component to the high frequency component.

Nonlinear parameters include but are not limited to: SD1, SD2, SD2/SD1, $\alpha1$, $\alpha2$, Lyapunov exponent, complexity parameters (C0 complexity, C1 complexity, C2 complexity), correlation dimension parameters (number of phase points, embedding dimension, delay time), and entropy parameters (sample entropy, approximate entropy, fuzzy entropy). Wherein, SD1 is a distance between two points with the longest distance in scatter plot area perpendicular to a X=Y direction, SD2 is a distance between two points with the longest distance in the scatter plot area in the X=Y direction, and SD2/SD1 is a ratio of SD2 to SD1. $\alpha1$ is a slope of a fitted straight line of a first part (the 1st point to the 11th point) of detrended fluctuation analysis of a HRV curve, $\alpha2$ is a slope of a fitted straight line of a second part (the 12th point to the last point) of the detrended fluctuation analysis of the HRV curve. The Lyapunov exponent is used to determine a chaotic index of a system, which represents average exponential divergence rate of adjacent trajectories in the phase space of the heart rate RR interval time series. Complexity reflects the rate at which new patterns appear in the heart rate RR interval time series as the length increases. It is defined as the proportion of random components in the time series. The larger the value, the higher the proportion of random components in the time series, that is, the higher the complexity of embodiments of the system, and vice versa. Complexity parameters include: C0 complexity, C1 complexity, and C2 complexity. Correlation dimension is based on a concept of phase space reconstruction to analyze nonlinear characteristics of the heart rate RR interval time series. Correlation dimension parameters include: the number of phase points in a phase space structure, the embedding dimension, and the delay time. Entropy represents regularity of the heart rate RR interval time series. The lower an entropy value, the more predictable and regular a signal of the RR interval time series is, and the higher the entropy value, the more random and unpredictable the RR interval time series is. Entropy parameters include: sample entropy, approximate entropy, and fuzzy entropy.

In some embodiments, the depression risk assessment device 30 includes a second data interface, a second processor and a second memory. The depression risk assessment device 30 may be a computer, or other electronic device including the above components, wherein the second processor is configured to drive the second data interface to receive the heart rate parameters and HRV characteristic parameters transmitted by the integration and calculation device 20.

In other examples, the depression risk assessment device 30 and the integration and calculation device 20 may also be the same computer, that is, the second data interface is an internal data transmission channel in the computer for transmitting data between different software, the first processor and the second processor are the same processor, the first memory and the second memory are the same memory, and functions of the depression risk assessment device 30 and the integration and calculation device 20 are respectively processed by different software programs running in the computer.

The depression screening model runs in the depression risk assessment device 30, which may be a scientific or engineering model constructed using a mathematical logic method and a mathematical language, or various machine learning models constructed using a computer language, including: neural network model, support vector machine model and genetic algorithm model. In the embodiment of the present application, the depression screening model is a mathematical structure and/or a machine learning model expressed by the inventor in a mathematical language and/or a computer language, based on an objective comparison relationship between the heart rate parameters and HRV characteristic parameters of depression patients and the heart rate parameters and HRV characteristic parameter big data samples of the general population, or further, in combination with the inventor's reference to change rules between the heart rate parameters and HRV characteristic parameters of depression patients in different test processes. This mathematical structure and/or machine learning model is a linear and/or nonlinear relationship structure of a certain system expressed with the help of mathematical symbols and/or the computer language.

In some embodiments, the depression screening model is configured to perform a first data comparison between the heart rate parameters and the HRV characteristic parameters in each test process and the sample data in the preset database based on the relationship between the heart rate parameters and HRV characteristic parameters of depression patients and the heart rate parameters and HRV characteristics of the general population; optionally. In some embodiments, when a comparison result of each specific parameter in the heart rate parameters and HRV characteristic parameters is greater than and/or less than a set threshold, a first comparison result is considered to be abnormal, wherein above judgment criteria is preset in the depression screening model.

In the embodiment of the present application, the first risk index is obtained by statistically analyzing each abnormal first comparison result. This statistical method may be to count number of the abnormal first comparison results, and the larger the number, the greater the first risk index. In other examples, certain weights may be assigned to different heart rate parameters or HRV characteristic parameters to calculate the first risk index.

The above first comparison is based on a rule that parasympathetic nerve regulation ability of depression patients is reduced compared with the general population, and their HRV characteristic parameters will also be reduced accordingly. Specifically, some experiments show that parameters such as SDNN, RMSSD and the like are reduced, while HF parameters are increased, and LF, LF/HF and the like are reduced.

In some embodiments, the heart rate parameters specifically include: a first heart rate parameter detected and obtained when the subject completes the normal breathing in the sitting posture; a second heart rate parameter detected and obtained when the subject completes the deep breathing in the sitting posture; a third heart rate parameter detected and obtained when the subject completes the normal breathing in the standing posture; a fourth heart rate parameter detected and obtained when the subject completes the deep breathing in the standing posture; the HRV characteristic parameters specifically include: a first HRV characteristic parameter detected and obtained when the subject completes the normal breathing in the sitting posture; a second HRV characteristic parameter detected and obtained when the subject completes the deep breathing in the sitting posture; a third HRV characteristic parameter detected and obtained when the subject completes the normal breathing in the standing posture; a fourth HRV characteristic parameter detected and obtained when the subject completes the deep breathing in the standing posture.

In other examples, the above-mentioned heart rate parameters and HRV characteristic parameters may also include parameters detected and obtained when the subject completes normal breathing and deep breathing in a lying posture, that is, 6 groups of parameters are included, or still 4 groups of parameters are included, that is, the sitting posture or the standing posture may be replaced by the lying posture.

The depression screening model is configured to obtain deviation data obtained by at least one of the following second data comparisons, according to change rules of the heart rate parameters and HRV characteristic parameters of depression patients in different test stages: the second heart rate parameter and the first heart rate parameter, the third heart rate parameter and the first heart rate parameter, the fourth heart rate parameter and the second heart rate parameter, the fourth heart rate parameter and the third heart rate parameter, the second HRV characteristic parameter and the first HRV characteristic parameter, the third HRV characteristic parameter and the first HRV characteristic parameter, the fourth HRV characteristic parameter and the second HRV characteristic parameter, the fourth HRV characteristic parameter and the third HRV characteristic parameter.

Figure 3:
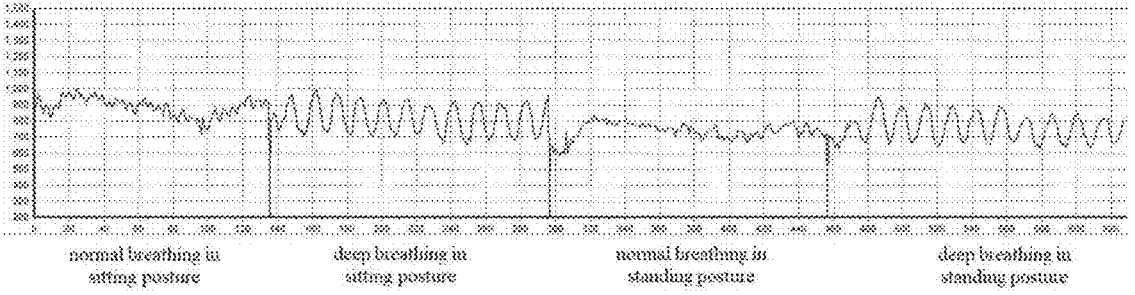
FIG. 3 is a schematic diagram of a heart rate spectrum of normal people.

As shown in FIGS. 3 and 4, the inventor found that not only do depression patients have differences in heart rate parameters and HRV characteristic parameters from the general population in each test step, but there are also corresponding differences in a change state between each test process. For example, when switching from the normal breathing in the sitting posture to the normal breathing in the standing posture, heart rate of the general population increases, while that of depression patients may not increase. Additionally, for example, when switching from the deep breathing in the sitting posture to the deep breathing in the standing posture, due to the increase in heart rate, the variance SDNN in the HRV characteristic parameters of the general population decreases, while the variance SDNN of depression patients may not decrease.

The depression screening model is also configured to perform a second data comparison between at least one of the deviation data and sample data in a preset database; and is also configured to obtain a second risk index according to each abnormal second comparison result. The statistical method may be to count number of the abnormal second comparison results. The larger the number, the greater the second risk index. In other examples, different weights may be assigned to different comparison results for comparisons of different heart rate parameters or HRV characteristic parameters.

The sample data in the preset database may be some specific deviation values to reflect a change range, or zero to reflect whether it changes, or whether it changes according to rule of getting higher or lower.

The depression screening model also obtains the depression risk index of the subject according to the first risk index and the second risk index. In some embodiments, the depression risk index may be obtained based on a sum of the first risk index and the second risk index. The first risk index and the second risk index may also be calculated by being assigned corresponding weighted values respectively.

In a specific example, taking only the following HRV characteristic parameters as an example for measurement, specific algorithm rules of the depression screening model are as follows: (1) The frequency domain parameter LF during the deep breathing in the sitting posture is compared with the data 1200 calculated by big data. If it is greater than 1200, the first risk index X1 is 0 point; if it is not greater than 1200, the first risk index X1 is 1 point. (2) The frequency domain parameter LF during the deep breathing in the standing posture is compared with the data 1200 calculated by the big data. If it is greater than 1200, the first risk index X2 is 0 point; if it is not greater than 1200, the first risk index X2 is 1 point. (3) The time domain parameter RMSSD during the normal breathing in the sitting posture is compared with the time domain parameter RMSSD of the normal breathing in the standing posture. If the deviation data obtained by the comparison is greater than zero, it is normal; if it is not greater than zero, it is abnormal, that is, the time domain parameter RMSSD must be reduced when adjusting from the normal breathing in the sitting posture to normal breathing in the standing posture; if it is reduced, the second risk index X3 is 0 point, and if it is not reduced, the second risk index X3 is 1 point. (4) The time domain parameter RMSSD during the deep breathing in the sitting posture is compared with the time domain parameter RMSSD during the deep breathing in the standing posture. If the deviation data obtained by the comparison is greater than zero, it is normal; if it is not greater than zero, it is abnormal, that is, the time domain parameter RMSSD must be reduced when adjusting from the deep breathing in the sitting posture to the deep breathing in the standing posture; if it is reduced, the second risk index X4 is 0 point, and if it is not reduced, the second risk index X4 is 1 point. (5) The nonlinear parameter SD1 during the normal breathing in the sitting posture is compared with the nonlinear parameter SD1 during the normal breathing in the standing posture. If the deviation data obtained by the comparison is greater than zero, it is normal; if it is not greater than zero, it is abnormal, that is, the nonlinear parameter SD1 must be reduced when adjusting from the normal breathing in the sitting posture to the normal breathing in the standing posture; if it is reduced, the second risk index X5 is 0 point; if it is not reduced, the second risk index X5 is 1 point. (6) The nonlinear parameter SD1 during the deep breathing in the sitting posture is compared with the nonlinear parameter SD1 during the deep breathing in the standing posture. If the deviation data obtained by the comparison is greater than zero, it is normal; if it is not greater than zero, it is abnormal, that is, the nonlinear parameter SD1 must be reduced when adjusting from the deep breathing in the sitting posture to the deep breathing in the standing posture; if it is reduced, the second risk index X6 is 0 point, and if it is not reduced, the second risk index X6 is 1 point.

According to the comparison of the above parameters, the first risk indices: X1, X2 and the second risk indices: X3, X4, X5, X6 are obtained, the depression risk index of the subject is:

$$\text{Depression Risk Index} = X1 + X2 + X3 + X4 + X5 + X6.$$

Healthy people: Depression risk index is 0 point; severe depression: Depression risk index is 6 points; mild and moderate depression: Depression risk index is between 1-5 points.

As shown in a table below, using the above HRV characteristic parameters, the inventor selected 12 subjects for objective screening of depression, and compared with clinical diagnosis results of doctors, it may be found that results of the objective screening have a very high accuracy. If more HRV parameters are selected, and the judgment rules of a depression diagnosis model in the example are further increased according to the change rule of the HRV parameters, embodiments of the system for screening depression according to the embodiment of the present application will also have more accurate objective screening results for depression.

| Patient number | Gender | Age | Doctor's diagnosis result | Objective screening result | Time domain parameter RMSSD(normal breathing in sitting posture) | Time domain parameter RMSSD(deep breathing in sitting posture) | Time domain parameter RMSSD(normal breathing in standing posture) | Time domain parameter RMSSD(deep breathing in standing posture) |
|---|---|---|---|---|---|---|---|---|
| 1 | Female | 25 | Healthy people | Healthy | 32.95 | 45.28 | 22.86 | 36.90 |
| 2 | Male | 42 | Healthy people | Healthy | 17.16 | 31.67 | 10.78 | 31.47 |
| 3 | Female | 38 | Healthy people | Healthy | 48.61 | 51.70 | 14.97 | 36.18 |
| 4 | Male | 28 | Mild depression | Mild depression | 42.14 | 44.65 | 38.40 | 46.27 |
| 5 | Female | 24 | Mild depression | Mild depression | 41.47 | 61.73 | 42.21 | 56.99 |
| 6 | Female | 57 | Mild depression | Mild depression | 23.33 | 63.96 | 27.02 | 50.19 |
| 7 | Male | 28 | Moderate depression | Moderate depression | 27.94 | 68.86 | 28.54 | 47.52 |
| 8 | Male | 24 | Moderate depression | Moderate depression | 12.26 | 39.55 | 22.79 | 31.43 |
| 9 | Male | 23 | Moderate depression | Moderate depression | 52.44 | 47.00 | 47.43 | 45.56 |

-continued

| Patient number | Gender | Age | Doctor's diagnosis result | Objective screening result | Time domain parameter RMSSD(normal breathing in sitting posture) | Time domain parameter RMSSD(deep breathing in sitting posture) | Time domain parameter RMSSD(normal breathing in standing posture) | Time domain parameter RMSSD(deep breathing in standing posture) |
|---|---|---|---|---|---|---|---|---|
| 10 | Female | 16 | Severe depression | Severe depression | 14.33 | 13.40 | 19.30 | 13.81 |
| 11 | Female | 16 | Severe depression | Severe depression | 19.08 | 15.01 | 26.48 | 24.30 |
| 12 | Female | 16 | Severe depression | Severe depression | 26.73 | 20.07 | 28.60 | 28.97 |

| Frequency domain parameter LF(deep breathing in sitting posture) | Frequency domain parameter LF(deep breathing in standing posture) | Nonlinear parameter SD1 (normal breathing in sitting posture) | Nonlinear parameter SD1 (deep breathing in sitting posture) | Nonlinear parameter SD1 (normal breathing in standing posture) | Nonlinear parameter SD1 (deep breathing in standing posture) |
|---|---|---|---|---|---|
| 7496.01 | 6014.44 | 23.39 | 32.11 | 16.24 | 26.17 |
| 2299.29 | 1646.20 | 12.17 | 22.46 | 7.65 | 22.32 |
| 7650.13 | 4485.10 | 34.51 | 36.68 | 10.61 | 25.66 |
| 5062.57 | 5043.73 | 29.91 | 31.67 | 27.33 | 32.83 |
| 4394.77 | 1658.55 | 29.42 | 43.79 | 29.99 | 40.44 |
| 870.07 | 577.23 | 16.54 | 45.37 | 19.20 | 35.61 |
| 4343.10 | 7962.63 | 19.82 | 48.91 | 20.29 | 33.70 |
| 852.71 | 397.55 | 8.69 | 28.05 | 16.17 | 22.28 |
| 3251.01 | 2675.84 | 37.22 | 33.33 | 33.77 | 32.33 |
| 613.86 | 231.15 | 10.16 | 9.49 | 13.69 | 9.78 |
| 808.80 | 303.12 | 13.52 | 10.64 | 18.78 | 17.22 |
| 1072.75 | 117.44 | 18.96 | 14.22 | 20.29 | 20.53 |

In some embodiments, the first risk indices X1, X2 and the second risk indices X3, X4, X5, X6 obtained in the above specific example are used as 6 input parameters of a machine learning model such as a neural network, a support vector machine and the like, and the doctor's diagnosis result Y is used as an output parameter of the machine learning model such as a neural network, a support vector machine and the like, and then the model is trained on collected clinical big data samples. In actual application, the above 6 risk indices X1, X2, X3, X4, X5, X6 are input into the trained machine learning model to output the depression risk index of the subject. In the above example, a data set with patient numbers 1, 2, 4, 5, 7, 8, 10, 11 may be used as a training sample set of the machine learning model, and the data set with patient numbers 3, 6, 9, 12 may be used as a test sample set of the machine learning model, and a prediction classification result of the machine learning model also have a fairly high accuracy.

In some embodiments, original sampling indicators in the above specific example: gender, age, time domain parameter RMSSD (normal breathing in the sitting posture), time domain parameter RMSSD (deep breathing in the sitting posture), time domain parameter RMSSD (normal breathing in the standing posture), time domain parameter RMSSD (deep breathing the a standing posture), frequency domain parameter LF (deep breathing in the sitting posture), frequency domain parameter LF (deep breathing in a standing posture), nonlinear parameter SD1 (normal breathing in the sitting posture), nonlinear parameter SD1 (deep breathing in the sitting posture), nonlinear parameter SD1 (normal breathing in the standing posture), nonlinear parameter SD1 (deep breathing in the standing posture) may be directly used as input parameters of the machine learning model; the doctor's diagnosis result Y may be used as the output parameter of the machine learning model; and the model may then be trained and tested, it also has a fairly high accuracy.

In some embodiments, the breathing detection device 50 includes a breathing detection module, which is configured to detect breathing data of the subject during the test processes. The doctor cannot know the subject's breathing status intuitively through observation, however the doctor may know whether the subject has completed the test actions as required by checking the breathing data. The breathing detection device may be tied to the subject's abdomen in a form of a belt to detect the subject's breathing data by detecting rise and fall of the subject's abdomen.

In some embodiments, the action standardization scoring device 60 is connected to the breathing detection device 50, and obtains the breathing data detected by the breathing detection device 50, and analyzes the breathing data to obtain a calm relaxation degree and/or breathing synchronization rate of the subject in each test stage, and obtains an action standardization score of the subject in each test stage according to the calm relaxation degree and/or the breathing synchronization rate. The better the calm relaxation degree during the normal breathing, the higher the score; the better the breathing synchronization rate during the deep breathing, the higher the score. If the calm relaxation degree during the normal breathing is poor, it means that the subject did not keep calm and relaxed according to test action requirements, so the action standardization score is low; if the breathing synchronization rate during the deep breathing is poor, it means that the subject did not take deep breaths according to the test action requirements, so the action standardization score is low.

The calm relaxation degree is used to indicate calmness of the body. Usually, the subject may maintain the calmness of the body through some external means, such as keeping calm and motionless, with the subject's hands on the knees, or if standing, the subject's hands are on a fixed object. In some embodiments, the calm relaxation degree may be detected by detecting whether a fluctuation interval between respiratory peaks is regular. The breathing synchronization rate is used to indicate whether the breathing interval of the subject is synchronized with a cycle and time point of a guiding instruction when the subject is taking a deep breath. The guiding instruction is used to guide the subject's deep breathing rhythm. When the action standardization score of one of the test processes is lower than a certain level, the subject needs to be asked to repeat the test process, or repeat the entire test processes.

In the system for objectively screening depression according to the embodiment of the present application, innovative test methods and steps make it easier for patients to standardize an operation, with good repeatability and standardization, and may be completed by everyone. In addition, compared with a traditional method of evaluating depression level by relying on a single indicator in each test stage, which requires a large amount of big data samples, has a low classification accuracy and poor robustness, the embodiment of the present application only needs a small amount of data samples to obtain a very high judgment and classification accuracy. Although each person's heart rate signal is different, the embodiment of the present application combines comparative change trend of each person between each test stage to make a more accurate assessment of the depression level of the subject, and all test actions may be automatically judged by the sensor whether the action is standardized, with strong robustness and wide adaptability.

Embodiment 2

Corresponding to the system of the first embodiment, the second embodiment provides a method of objectively screening depression, and as shown in FIG. 5, the method includes the following steps:

Step S501: acquiring electrocardiogram (ECG) signals of a subject when the subject completes test processes, wherein the test processes include: normal breathing in a first posture, deep breathing in the first posture, normal breathing in a second posture, and deep breathing in the second posture;

Step S502: obtaining the ECG signals from an ECG signal acquisition device, and integrating and calculating the ECG signals to obtain heart rate parameters and HRV characteristic parameters of the subject in each of the test processes, wherein the HRV characteristic parameters include at least one of the following: time domain parameters, frequency domain parameters, and nonlinear parameters; and Step S503: inputting the heart rate parameters and the HRV characteristic parameters in each of the test processes into a depression screening model to obtain a depression risk index of the subject.

Wherein, depression screening results include at least one of the following: normal, mild depression, moderate depression, severe depression.

In an optional embodiment, the first posture includes any one of the following: lying posture, sitting posture, standing posture; the second posture includes any one of the following: lying posture, sitting posture, standing posture; the first posture is different from the second posture.

In an optional embodiment, the test processes further include: normal breathing in a third posture, and deep breathing in the third posture; the third posture includes any of the following: lying posture, sitting posture, standing posture; and the third posture is different from the first posture and the second posture.

In an optional embodiment, inputting the heart rate parameters and the HRV characteristic parameters in each of the test processes into a depression screening model to obtain a depression risk index of the subject includes: performing a first data comparison between the heart rate parameters and the HRV characteristic parameters in each of the test processes and sample data in a preset database; obtaining a first risk index according to each abnormal first comparison result; and obtaining the depression risk index of the subject according to the first risk index.

In an optional embodiment, the heart rate parameters include: a first heart rate parameter detected and obtained when the subject completes the normal breathing in the sitting posture; a second heart rate parameter detected and obtained when the subject completes the deep breathing in the sitting posture; a third heart rate parameter detected and obtained when the subject completes the normal breathing in the standing posture; a fourth heart rate parameter detected and obtained when the subject completes the deep breathing in the standing posture; the HRV characteristic parameters include: a first HRV characteristic parameter detected and obtained when the subject completes the normal breathing in the sitting posture; a second HRV characteristic parameter detected and obtained when the subject completes the deep breathing in the sitting posture; a third HRV characteristic parameter detected and obtained when the subject completes the normal breathing in the standing posture; a fourth HRV characteristic parameter detected and obtained when the subject completes the deep breathing in the standing posture;

In embodiments the method further includes:

obtaining deviation data obtained by at least one of the following comparisons: the second heart rate parameter and the first heart rate parameter, the third heart rate parameter and the first heart rate parameter, the fourth heart rate parameter and the second heart rate parameter, the fourth heart rate parameter and the third heart rate parameter, the second HRV characteristic parameter and the first HRV characteristic parameter, the third HRV characteristic parameter and the first HRV characteristic parameter, the fourth HRV characteristic parameter and the second HRV characteristic parameter, the fourth HRV characteristic parameter and the third HRV characteristic parameter; performing a second data comparison between at least one of the deviation data and sample data in a preset database; obtaining a second risk index according to each abnormal second comparison result, and obtaining the depression risk index of the subject according to the first risk index and the second risk index.

In an embodiment, the method further includes a following step: detecting the breathing data of the subject during the test processes.

In an optional embodiment, after detecting the breathing data of the subject during the test, the following steps are also included: obtaining the calm relaxation degree and/or the breathing synchronization rate of the subject in each test stage according to the breathing data; and obtaining an action standardization score of the subject in each test stage according to the calm relaxation degree and/or the breathing synchronization rate.

In an optional embodiment, each abnormal first comparison result includes that the first comparison result is greater than and/or less than a set threshold; and each abnormal second comparison result includes that the second comparison result is greater than and/or less than a set threshold.

In an optional embodiment, obtaining the ECG signals of the subject when the subject completes the test processes includes: connecting to the subject through a sensor and acquiring the ECG signals of the subject when the subject completes a test action; filtering the ECG signals sent by the sensor, converting the filtered ECG signals into digital signals through an AD sampling circuit to obtain the ECG signals.

In the method of objectively screening depression according to the embodiment of the present application, innovative test methods and steps make it easier for patients to standardize an operation, with good repeatability and standardization, and may be completed by everyone. In addition, compared with a traditional method of evaluating depression level by relying on a single indicator in each test stage, which requires a large amount of big data samples, has a low classification accuracy and poor robustness, the embodiment of the present application only needs a small amount of data samples to obtain a very high judgment and classification accuracy. Although each person's heart rate signal is different, the embodiment of the present application combines comparative change trend of each person between each test stage to make a more accurate assessment of the depression level of the subject, and all test actions may be automatically judged by the sensor whether the action is standardized, with strong robustness and wide adaptability.

Embodiment 3

Figure 6:
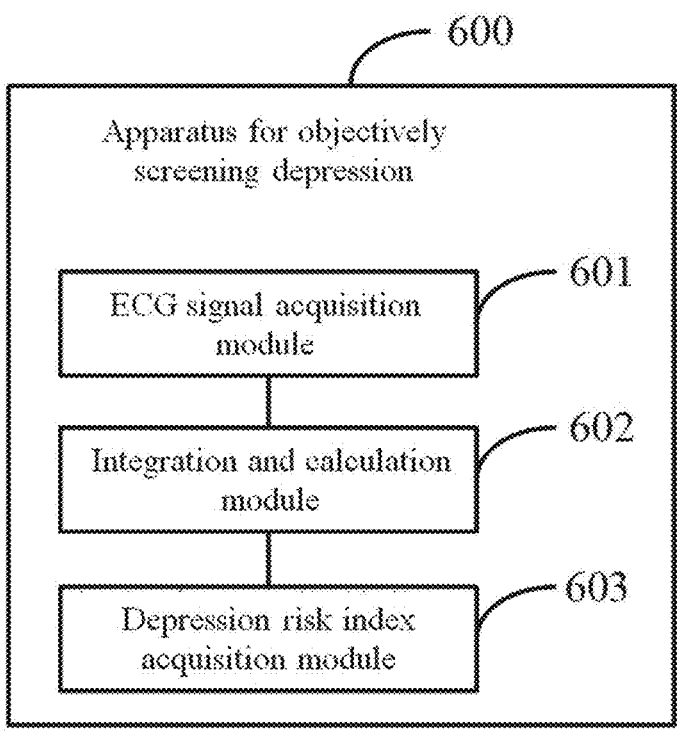
FIG. 6 is a schematic structural diagram of an apparatus for objectively screening depression according to an embodiment.

Corresponding to the method of the second embodiment, the embodiment of the present application further provides an apparatus for objectively screening depression, as shown in FIG. 6, the apparatus 600 includes: an electrocardiogram (ECG) signal acquisition module 601 configured to acquire ECG signals of a subject when the subject completes test processes, wherein the test processes include: normal breathing in a first posture, deep breathing in the first posture, normal breathing in a second posture, and deep breathing in the second posture; an integration and calculation module 602 configured to obtain the ECG signals from the ECG signal acquisition module, and integrate and calculate the ECG signals to obtain heart rate parameters and HRV characteristic parameters of the subject in each of the test processes, wherein the HRV characteristic parameters include at least one of the following: time domain parameters, frequency domain parameters, and nonlinear parameters; and a depression risk index acquisition module 603 configured to input the heart rate parameters and the HRV characteristic parameters in each of the test processes into a depression screening model to obtain a depression risk index of the subject.

In an optional embodiment, depression screening results include at least one of the following: normal, mild depression, moderate depression, severe depression.

In an optional embodiment, the first posture includes any one of the following: lying posture, sitting posture, standing posture; the second posture includes any one of the following: lying posture, sitting posture, standing posture; the first posture is different from the second posture.

In an optional embodiment, the test processes further include: normal breathing in a third posture, and deep breathing in the third posture; the third posture includes any of the following: lying posture, sitting posture, standing posture; and the third posture is different from the first posture and the second posture.

In an optional embodiment, the depression risk index acquisition module 603 includes: a first comparison unit configured to perform a first data comparison between the heart rate parameters and the HRV characteristic parameters in each of the test processes and sample data in a preset database; a first risk index acquisition unit configured to obtain a first risk index according to each abnormal first comparison result; and a first depression risk index acquisition unit configured to obtain the depression risk index of the subject according to the first risk index.

In an optional embodiment, the heart rate parameters include: a first heart rate parameter detected and obtained when the subject completes the normal breathing in the sitting posture; a second heart rate parameter detected and obtained when the subject completes the deep breathing in the sitting posture; a third heart rate parameter detected and obtained when the subject completes the normal breathing in the standing posture; a fourth heart rate parameter detected and obtained when the subject completes the deep breathing in the standing posture; the HRV characteristic parameters include: a first HRV characteristic parameter detected and obtained when the subject completes the normal breathing in the sitting posture; a second HRV characteristic parameter detected and obtained when the subject completes the deep breathing in the sitting posture; a third HRV characteristic parameter detected and obtained when the subject completes the normal breathing in the standing posture; a fourth HRV characteristic parameter detected and obtained when the subject completes the deep breathing in the standing posture; the apparatus 600 further includes: a deviation data acquisition unit configured to obtain deviation data obtained by at least one of the following comparisons: the second heart rate parameter and the first heart rate parameter, the third heart rate parameter and the first heart rate parameter, the fourth heart rate parameter and the second heart rate parameter, the fourth heart rate parameter and the third heart rate parameter, the second HRV characteristic parameter and the first HRV characteristic parameter, the third HRV characteristic parameter and the first HRV characteristic parameter, the fourth HRV characteristic parameter and the second HRV characteristic parameter, the fourth HRV characteristic parameter and the third HRV characteristic parameter; a second comparison unit configured to perform a second data comparison between at least one of the deviation data and sample data in a preset database; a second depression risk index acquisition unit configured to obtain a second risk index according to each abnormal second comparison result, and to obtain the depression risk index of the subject according to the first risk index and the second risk index.

In an optional embodiment, the apparatus 600 further includes: a respiratory data detection module configured to detect the breathing data of the subject during the test.

In an optional embodiment, the apparatus 600 further includes: a calm relaxation degree acquisition module configured to obtain the calm relaxation degree of the subject in the normal breathing test stage according to the breathing data; a breathing synchronization rate acquisition module configured to obtain the breathing synchronization rate of the subject in the deep breathing test stage according to the breathing data; an action standardization score acquisition module configured to obtain an action standardization score of the subject in each test stage according to the calm relaxation degree and/or the breathing synchronization rate.

In an optional embodiment, each abnormal first comparison result includes that the first comparison result is greater than and/or less than a set threshold; and each abnormal second comparison result includes that the second comparison result is greater than and/or less than a set threshold.

In an optional embodiment, the ECG signal acquisition module 601 includes: an ECG signal processing unit configured to connect to the subject through a sensor and to acquire the ECG signals of the subject when the subject completes the test action; and a filter unit configured to filter the ECG signals sent by the sensor, and to convert the filtered ECG signals into digital signals through an AD sampling circuit to obtain the ECG signals.

Embodiment 4

The present application also provides an electronic device, which includes at least one memory and at least one processor; and a computer program product (non-transitory computer readable storage medium having instructions, which when executed by a processor, perform actions)

stored in the memory and executable by the processor, wherein the processor implements the following steps when executing the computer program: acquiring electrocardiogram (ECG) signals of a subject when the subject completes test processes, wherein the test processes include: normal breathing in a first posture, deep breathing in the first posture, normal breathing in a second posture, and deep breathing in the second posture; obtaining the ECG signals from an ECG signal acquisition device, and integrating and calculating the ECG signals to obtain heart rate parameters and HRV characteristic parameters of the subject in each of the test processes, wherein the HRV characteristic parameters include at least one of the following: time domain parameters, frequency domain parameters, and nonlinear parameters; and inputting the heart rate parameters and the HRV characteristic parameters in each of the test processes into a depression screening model to obtain a depression risk index of the subject.

In some embodiments, depression screening results include at least one of the following: normal, mild depression, moderate depression, severe depression.

In some embodiments, the first posture includes any one of the following: lying posture, sitting posture, standing posture; the second posture includes any one of the following: lying posture, sitting posture, standing posture; the first posture is different from the second posture.

In some embodiments, the test processes further include: normal breathing in a third posture, and deep breathing in the third posture; the third posture includes any of the following: lying posture, sitting posture, standing posture; and the third posture is different from the first posture and the second posture.

In some embodiments, when processor executes the computer program, the following steps are also implemented: performing a first data comparison between the heart rate parameters and the HRV characteristic parameters in each of the test processes and sample data in a preset database; obtaining a first risk index according to each abnormal first comparison result; and obtaining the depression risk index of the subject according to the first risk index.

In some embodiments, the heart rate parameters include: a first heart rate parameter detected and obtained when the subject completes the normal breathing in the sitting posture; a second heart rate parameter detected and obtained when the subject completes the deep breathing in the sitting posture; a third heart rate parameter detected and obtained when the subject completes the normal breathing in the standing posture; a fourth heart rate parameter detected and obtained when the subject completes the deep breathing in the standing posture; the HRV characteristic parameters include: a first HRV characteristic parameter detected and obtained when the subject completes the normal breathing in the sitting posture; a second HRV characteristic parameter detected and obtained when the subject completes the deep breathing in the sitting posture; a third HRV characteristic parameter detected and obtained when the subject completes the normal breathing in the standing posture; a fourth HRV characteristic parameter detected and obtained when the subject completes the deep breathing in the standing posture; when the processor executes the computer program, the following steps are also implemented: obtaining deviation data obtained by at least one of the following comparisons: the second heart rate parameter and the first heart rate parameter, the third heart rate parameter and the first heart rate parameter, the fourth heart rate parameter and the second heart rate parameter, the fourth heart rate parameter and the third heart rate parameter, the second HRV characteristic parameter and the first HRV characteristic parameter, the third HRV characteristic parameter and the first HRV characteristic parameter, the fourth HRV characteristic parameter and the second HRV characteristic parameter, the fourth HRV characteristic parameter and the third HRV characteristic parameter; performing a second data comparison between at least one of the deviation data and sample data in a preset database; obtaining a second risk index according to each abnormal second comparison result, and obtaining the depression risk index of the subject according to the first risk index and the second risk index.

In some embodiments, when the processor executes the computer program, the following step is also implemented: detecting the breathing data of the subject during the test.

In some embodiments, when the processor executes the computer program, the following steps are also implemented: obtaining a calm relaxation degree and/or breathing synchronization rate of the subject in each test stage according to the breathing data; and obtaining an action standardization score of the subject in each test stage according to the calm relaxation degree and/or the breathing synchronization rate.

In some embodiments, each abnormal first comparison result includes that the first comparison result is greater than and/or less than a set threshold; and each abnormal second comparison result includes that the second comparison result is greater than and/or less than a set threshold.

In some embodiments, when the processor executes the computer program, the following steps are also implemented: connecting to the subject through a sensor and acquiring the ECG signals of the subject when the subject completes a test action; filtering the ECG signals sent by the sensor, converting the filtered ECG signals into digital signals through an AD sampling circuit to obtain the ECG signals.

Embodiment 5

The embodiment of the present application further provides a storage medium. In some embodiments, in this embodiment, the storage medium may be used to store program code executed by the method of objectively screening depression provided in the second embodiment.

In some embodiments, in this embodiment, the storage medium may be located in any computer terminal in a computer terminal group in a computer network, or in any mobile terminal in a mobile terminal group.

In some embodiments, in this embodiment, the storage medium is configured to store the program code for executing the following steps: acquiring electrocardiogram (ECG) signals of a subject when the subject completes test processes, wherein the test processes include: normal breathing in a first posture, deep breathing in the first posture, normal breathing in a second posture, and deep breathing in the second posture; obtaining the ECG signals from an ECG signal acquisition device, and integrating and calculating the ECG signals to obtain heart rate parameters and HRV characteristic parameters of the subject in each of the test processes, wherein the HRV characteristic parameters include at least one of the following: time domain parameters, frequency domain parameters, and nonlinear parameters; and inputting the heart rate parameters and the HRV characteristic parameters in each of the test processes into a depression screening model to obtain a depression risk index of the subject.

In some embodiments, depression screening results include at least one of the following: normal, mild depression, moderate depression, severe depression.

In some embodiments, the first posture includes any one of the following: lying posture, sitting posture, standing posture; the second posture includes any one of the following: lying posture, sitting posture, standing posture; the first posture is different from the second posture.

In some embodiments, the test processes further include: normal breathing in a third posture, and deep breathing in the third posture; the third posture includes any of the following: lying posture, sitting posture, standing posture; and the third posture is different from the first posture and the second posture.

In some embodiments, the storage medium is also configured to store the program code for executing the following steps: performing a first data comparison between the heart rate parameters and the HRV characteristic parameters in each of the test processes and sample data in a preset database; obtaining a first risk index according to each abnormal first comparison result; and obtaining the depression risk index of the subject according to the first risk index.

In some embodiments, the heart rate parameters include: a first heart rate parameter detected and obtained when the subject completes the normal breathing in the sitting posture; a second heart rate parameter detected and obtained when the subject completes the deep breathing in the sitting posture; a third heart rate parameter detected and obtained when the subject completes the normal breathing in the standing posture; a fourth heart rate parameter detected and obtained when the subject completes the deep breathing in the standing posture; the HRV characteristic parameters include: a first HRV characteristic parameter detected and obtained when the subject completes the normal breathing in the sitting posture; a second HRV characteristic parameter detected and obtained when the subject completes the deep breathing in the sitting posture; a third HRV characteristic parameter detected and obtained when the subject completes the normal breathing in the standing posture; a fourth HRV characteristic parameter detected and obtained when the subject completes the deep breathing in the standing posture; the storage medium is also configured to store program code for executing the following steps: obtaining deviation data obtained by at least one of the following comparisons: the second heart rate parameter and the first heart rate parameter, the third heart rate parameter and the first heart rate parameter, the fourth heart rate parameter and the second heart rate parameter, the fourth heart rate parameter and the third heart rate parameter, the second HRV characteristic parameter and the first HRV characteristic parameter, the third HRV characteristic parameter and the first HRV characteristic parameter, the fourth HRV characteristic parameter and the second HRV characteristic parameter, the fourth HRV characteristic parameter and the third HRV characteristic parameter; performing a second data comparison between at least one of the deviation data and sample data in a preset database; obtaining a second risk index according to each abnormal second comparison result, and obtaining the depression risk index of the subject according to the first risk index and the second risk index.

In some embodiments, the storage medium is also configured to store the program code for executing a following step: detecting the breathing data of the subject during the test processes.

In an optional embodiment, after detecting the breathing data of the subject during the test processes, the following steps are further included: obtaining calm relaxation degree and/or the breathing synchronization rate of the subject in each test stage according to the breathing data; and obtaining an action standardization score of the subject in each test stage according to the calm relaxation degree and/or the breathing synchronization rate.

In some embodiments, each abnormal first comparison result includes that the first comparison result is greater than and/or less than a set threshold; and each abnormal second comparison result includes that the second comparison result is greater than and/or less than a set threshold.

In some embodiments, the storage medium is also configured to store the program code for executing following steps: connecting to the subject through a sensor and acquiring the ECG signals of the subject when the subject completes a test action; filtering the ECG signals sent by the sensor, converting the filtered ECG signals into digital signals through an AD sampling circuit to obtain the ECG signals.

It should be understood that the embodiments of the present application are not limited to the precise structures described above and shown in the drawings, and various modifications and changes may be made without departing from the scope thereof. The scope of the embodiments of the present application is limited only by the attached claims.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements.

What is claimed:

1. A system for objectively screening depression, comprising:

an electrocardiogram signal acquisition device configured to acquire ECG signals of a subject when a subject completes test processes, wherein the test processes include: normal breathing in a first posture, deep breathing in the first posture, normal breathing in a second posture, and deep breathing in the second posture; the first posture includes any one of the following: lying posture, sitting posture, standing posture; the second posture includes any one of the following: lying posture, sitting posture, standing posture; and the first posture is different from the second posture;

an integration and calculation device configured to obtain the ECG signals from the ECG signal acquisition device, and integrate and calculate the ECG signals to obtain heart rate parameters and HRV characteristic parameters of the subject in each of the test processes, wherein the HRV characteristic parameters include at least one of the following: time domain parameters, frequency domain parameters, and nonlinear parameters; and a depression risk assessment device configured to input the heart rate parameters and the HRV characteristic parameters in each of the test processes into a depression screening model, wherein the depression screening model is configured to perform a first data comparison between the heart rate parameters and the HRV characteristic parameters in each of the test processes and sample data in a preset database, to obtain a first risk index according to each abnormal first comparison result, and to obtain the depression risk index of the subject according to the first risk index.

2. The system for objectively screening depression of claim 1, wherein, the heart rate parameters include:

a first heart rate parameter detected and obtained when the subject completes the normal breathing in the first posture;

a second heart rate parameter detected and obtained when the subject completes the deep breathing in the first posture;

a third heart rate parameter detected and obtained when the subject completes the normal breathing in the second posture;

a fourth heart rate parameter detected and obtained when the subject completes the deep breathing in the second posture;

the HRV characteristic parameters include:

a first HRV characteristic parameter detected and obtained when the subject completes the normal breathing in the first posture;

a second HRV characteristic parameter detected and obtained when the subject completes the deep breathing in the first posture;

a third HRV characteristic parameter detected and obtained when the subject completes the normal breathing in the second posture;

a fourth HRV characteristic parameter detected and obtained when the subject completes the deep breathing in the second posture;

the depression screening model is also configured to obtain deviation data obtained by at least one of the following comparisons:

the second heart rate parameter and the first heart rate parameter, the third heart rate parameter and the first heart rate parameter, the fourth heart rate parameter and the second heart rate parameter, the fourth heart rate parameter and the third heart rate parameter, the second HRV characteristic parameter and the first HRV characteristic parameter, the third HRV characteristic parameter and the first HRV characteristic parameter, the fourth HRV characteristic parameter and the second HRV characteristic parameter, the fourth HRV characteristic parameter and the third HRV characteristic parameter;

the depression screening model is configured to perform a second data comparison between at least one of the deviation data with the sample data in the preset database;

the depression screening model is further configured to obtain a second risk index according to each abnormal second comparison result, and to obtain the depression risk index of the subject according to the first risk index and the second risk index.

3. The system for objectively screening depression of claim 2, further comprising a breathing detection device including a breathing detection module, wherein the breathing detection module is configured to detect breathing data of the subject during the test processes.

4. The system for objectively screening depression of claim 3, further comprising an action standardization scoring device that is connected to the breathing detection device, and is configured to obtain calm relaxation degree of the subject in each normal breathing test stage and breathing synchronization rate of the subject in each deep breathing test stage according to the breathing data, and to obtain an action standardization score of the subject in each test stage according to the calm relaxation degree and/or the breathing synchronization rate.

5. The system for objectively screening depression of claim 2, wherein, the each abnormal first comparison result includes that the first comparison result is greater than and/or less than a set threshold;

the each abnormal second comparison result includes that the second comparison result is greater than and/or less than a set threshold.

6. The system for objectively screening depression of claim 1, wherein, the ECG signal acquisition device includes a sensor, an ECG signal processing circuit and an AD sampling circuit connected in sequence, the sensor is configured to connect to the subject and acquire the ECG signals of the subject when the subject completes test processes, the ECG signal processing circuit is integrated with a filter amplifier for filtering the ECG signals sent by the sensor, and the ECG signals after filtering are converted into digital signals by the AD sampling circuit and sent to the integration and calculation device;

the integration and calculation device includes a first data interface, a first processor and a first memory, the first processor is configured to drive the first data interface to receive the ECG signals, and to store the ECG signals in the first memory, and the first processor is further configured to integrate and calculate the ECG signals;

the depression risk assessment device includes a second data interface, a second processor and a second memory, the second processor is configured to drive the second data interface to receive the heart rate parameters and the HRV characteristic parameters, and store the heart rate parameters and the HRV characteristic parameters in the second memory, and the second processor is further configured to input the heart rate parameters and the HRV characteristic parameters in each of the test processes into the depression screening model; the time domain parameters include at least one of the following: MEAN_HR, MAX_HR, MIN_HR, STD_HR, MEAN, SDNN, SDSD, RMSSD, average NN, NN50, PNN50, NN20, PNN20, RANGE_NNI, CVSD and CVNNI;

the frequency domain parameters include at least one of the following: VLF, LF, HF, TP, pVLF, pLF, pHF, nLF, nHF and LF/HF;

the nonlinear parameters include at least one of the following: SD1, SD2, SD2/SD1, α1, α2, Lyapunov exponent, complexity parameters, correlation dimension parameters and entropy parameters;

wherein, the complexity parameters include at least one of the following: C0 complexity, C1 complexity, C2 complexity;

wherein, the correlation dimension parameters include at least one of the following:

number of phase points, embedding dimension, delay time;

wherein, the entropy parameters include at least one of the following: sample entropy, approximate entropy, fuzzy entropy.

7. An electronic device, comprising at least one memory and at least one processor; and a computer program product, comprising a computer readable hardware storage device having computer readable program code stored therein, said program code executable by a processor of a computer system to implement a method=when executing the computer program, the method comprising:

acquiring electrocardiogram signals of a subject when the subject completes test processes, wherein the test processes include: normal breathing in a first posture, deep breathing in the first posture, normal breathing in a second posture, and deep breathing in the second posture; the first posture includes any one of the following: lying posture, sitting posture, standing posture; the second posture includes any one of the following: lying posture, sitting posture, standing posture; and the first posture is different from the second posture; obtaining the ECG signals from an ECG signal acquisition device, and integrating and calculating the ECG signals to obtain heart rate parameters and HRV characteristic parameters of the subject in each of the test processes, wherein the HRV characteristic parameters include at least one of the following: time domain parameters, frequency domain parameters, and nonlinear parameters; and inputting the heart rate parameters and the HRV characteristic parameters in each of the test processes into a depression screening model, wherein the depression screening model is configured to perform a first data comparison between the heart rate parameters and the HRV characteristic parameters in each of the test processes and sample data in a preset database, to obtain a first risk index according to each abnormal first comparison result, and to obtain the depression risk index of the subject according to the first risk index.

8. A storage medium storing a computer instruction program, wherein, when the computer instruction program is executed by a processor, the processor implements following steps:

acquiring electrocardiogram signals of a subject when the subject completes test processes, wherein the test processes include: normal breathing in a first posture, deep breathing in the first posture, normal breathing in a second posture, and deep breathing in the second posture; the first posture includes any one of the following: lying posture, sitting posture, standing posture; the second posture includes any one of the following: lying posture, sitting posture, standing posture; and the first posture is different from the second posture; obtaining the ECG signals from an ECG signal acquisition device, and integrating and calculating the ECG signals to obtain heart rate parameters and HRV characteristic parameters of the subject in each of the test processes, wherein the HRV characteristic parameters include at least one of the following: time domain parameters, frequency domain parameters, and nonlinear parameters; and inputting the heart rate parameters and the HRV characteristic parameters in each of the test processes into a depression screening model, wherein the depression screening model is configured to perform a first data comparison between the heart rate parameters and the HRV characteristic parameters in each of the test processes and sample data in a preset database, to obtain a first risk index according to each abnormal first comparison result, and to obtain the depression risk index of the subject according to the first risk index.

\* \* \* \* \*